(12) United States Patent
Briggs et al.

(10) Patent No.: US 10,971,030 B2
(45) Date of Patent: Apr. 6, 2021

(54) REMOTE PHYSICAL TRAINING

(71) Applicant: International Business Machines Corporation, Armonk, NY (US)

(72) Inventors: Benjamin D. Briggs, Waterford, NY (US); Lawrence A. Clevenger, Rhinebeck, NY (US); Leigh Anne H. Clevenger, Rhinebeck, NY (US); Christopher J. Penny, Saratoga Springs, NY (US); Michael Rizzolo, Albany, NY (US); Aldis G. Sipolins, New York, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 700 days.

(21) Appl. No.: 15/416,046

(22) Filed: Jan. 26, 2017

(65) Prior Publication Data

US 2018/0207484 A1 Jul. 26, 2018

(51) Int. Cl.
*G09B 19/00* (2006.01)
*G09B 5/06* (2006.01)
*G06F 3/01* (2006.01)
*G16H 20/30* (2018.01)
*G16H 50/20* (2018.01)
*G16H 50/70* (2018.01)
*G16H 40/67* (2018.01)

(52) U.S. Cl.
CPC .......... *G09B 19/0038* (2013.01); *G06F 3/011* (2013.01); *G09B 5/06* (2013.01); *G16H 20/30* (2018.01); *G16H 40/67* (2018.01); *G16H 50/20* (2018.01); *G16H 50/70* (2018.01)

(58) Field of Classification Search
CPC ............ A63B 24/0075; A63B 24/0006; A63B 2024/0081; A63B 2024/0012; G06F 3/013; G06F 3/012; G06F 3/0482; G06F 3/011; G06T 13/40; G06T 2200/04; G06T 2207/30196; G09B 19/0038; G09B 5/06; G16H 20/30; G16H 50/70; G16H 50/20; G16H 40/67
See application file for complete search history.

(56) References Cited

U.S. PATENT DOCUMENTS

| 7,780,450 | B2 | 8/2010 | Tarry |
| 8,113,991 | B2 | 2/2012 | Kutliroff |
| 9,358,426 | B2 | 6/2016 | Aragones et al. |
| 2008/0090679 | A1* | 4/2008 | Browne ............. A63B 24/0003 473/422 |

(Continued)

OTHER PUBLICATIONS

Eaves et al., "The Short-Term Effects of Real-Time Virtual Reality Feedback on Motor Learning in Dance", Presence, 20 (1), 2011, pp. 62-77.

*Primary Examiner* — Nathan Hillery
(74) *Attorney, Agent, or Firm* — Cantor Colburn LLP; Anthony Curro

(57) ABSTRACT

A system and method perform remote physical training. The method includes receiving movements performed by an operator who is remotely located, and presenting the movements of the operator as movements performed by an avatar representing the operator in a virtual reality environment. The method also includes remotely monitoring the movements of the avatar, and providing real-time feedback on the movements to the operator.

9 Claims, 5 Drawing Sheets

(56) References Cited

U.S. PATENT DOCUMENTS

| | | | |
|---|---|---|---|
| 2009/0094535 A1* | 4/2009 | Bromenshenkel | A63F 13/10 |
| | | | 715/757 |
| 2009/0187389 A1* | 7/2009 | Dobbins | G06F 3/011 |
| | | | 703/6 |
| 2009/0278917 A1* | 11/2009 | Dobbins | G06F 3/011 |
| | | | 348/53 |
| 2009/0298650 A1* | 12/2009 | Kutliroff | A63B 71/0622 |
| | | | 482/8 |
| 2010/0060648 A1* | 3/2010 | Carter | A63F 13/12 |
| | | | 345/474 |
| 2010/0157018 A1* | 6/2010 | Lampotang | G06F 3/011 |
| | | | 348/36 |
| 2010/0248200 A1 | 9/2010 | Ladak et al. | |
| 2012/0183940 A1* | 7/2012 | Aragones | G06F 19/3481 |
| | | | 434/247 |
| 2013/0104058 A1* | 4/2013 | Bromenshenkel | G06F 3/01 |
| | | | 715/757 |
| 2013/0252216 A1* | 9/2013 | Clavin | G09B 19/0038 |
| | | | 434/257 |
| 2014/0287389 A1 | 9/2014 | Kallmann et al. | |
| 2015/0133820 A1 | 5/2015 | Zohar et al. | |
| 2017/0213473 A1* | 7/2017 | Ribeira | G06F 19/3456 |
| 2018/0124308 A1* | 5/2018 | Andreassen | G06F 16/783 |
| 2020/0013312 A1* | 1/2020 | Pregizer | G09B 19/0038 |

* cited by examiner

REMOTE PHYSICAL TRAINING

BACKGROUND

The present invention relates in general to virtual reality systems. More specifically, the present invention relates to virtual reality systems that use real-time multi-sensory feedback to implement a remote physical training methodology.

The phrase "virtual reality" refers to computer technologies that use software to generate realistic images, sounds, and other sensations for a user. A known configuration of a virtual reality system includes a head-mounted display with sensors to determine movement of the operator. Virtual reality systems can simulate a real environment and the user's physical presence in the simulated "real" environment based on the sensed movements. A person using a virtual reality system is typically able to "look around" the artificial world, move about in it, and interact with features or items that are depicted on the head-mounted display worn by the user.

SUMMARY

According to one or more embodiments of the present invention, a computer-implemented method of performing remote physical training includes receiving movements performed by an operator who is remotely located, and presenting the movements of the operator as movements performed by an avatar representing the operator in a virtual reality environment. The method also includes remotely monitoring the movements of the avatar, and providing real-time feedback on the movements to the operator.

According to one or more embodiments of the present invention, a computer system to perform remote physical training includes a virtual reality system configured to determine movements of an operator and present the movements as movements performed by an avatar representing the operator in a virtual reality environment. The computer system further includes a trainer system, remote from the virtual reality system, configured to obtain the movements of the avatar and provide real-time feedback to the operator through the virtual reality system of the operator.

According to one or more embodiments of the present invention, a computer program product performs remote physical training. The computer program product includes a computer readable storage medium having program instructions embodied therewith. The program instructions are executable by a processor to perform a method that includes determining movements performed by an operator. The method also includes presenting the movements of the operator as movements performed by an avatar representing the operator in a virtual reality environment, providing the movements of the avatar to a trainer system for remote monitoring, obtaining real-time feedback on the movements from the trainer system and providing the real-time feedback to the operator.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

As previously noted, a virtual reality environment is a simulated three-dimensional environment with which an operator can interact. Virtual reality is increasingly used to enhance applications that typically involved two-dimensional images. For example, virtual gaming, virtual tourism, virtual campus visits, and virtual sporting events allow an operator to feel as though they are experiencing the game environment, tourist destination, college campus, or sporting event firsthand. Embodiments of the systems and methods detailed herein relate to remote physical training using a virtual reality environment. The virtual reality system includes communication components to facilitate group training in a virtual environment, feedback regarding the training, and dynamic adjustment of the training.

Figure 1:
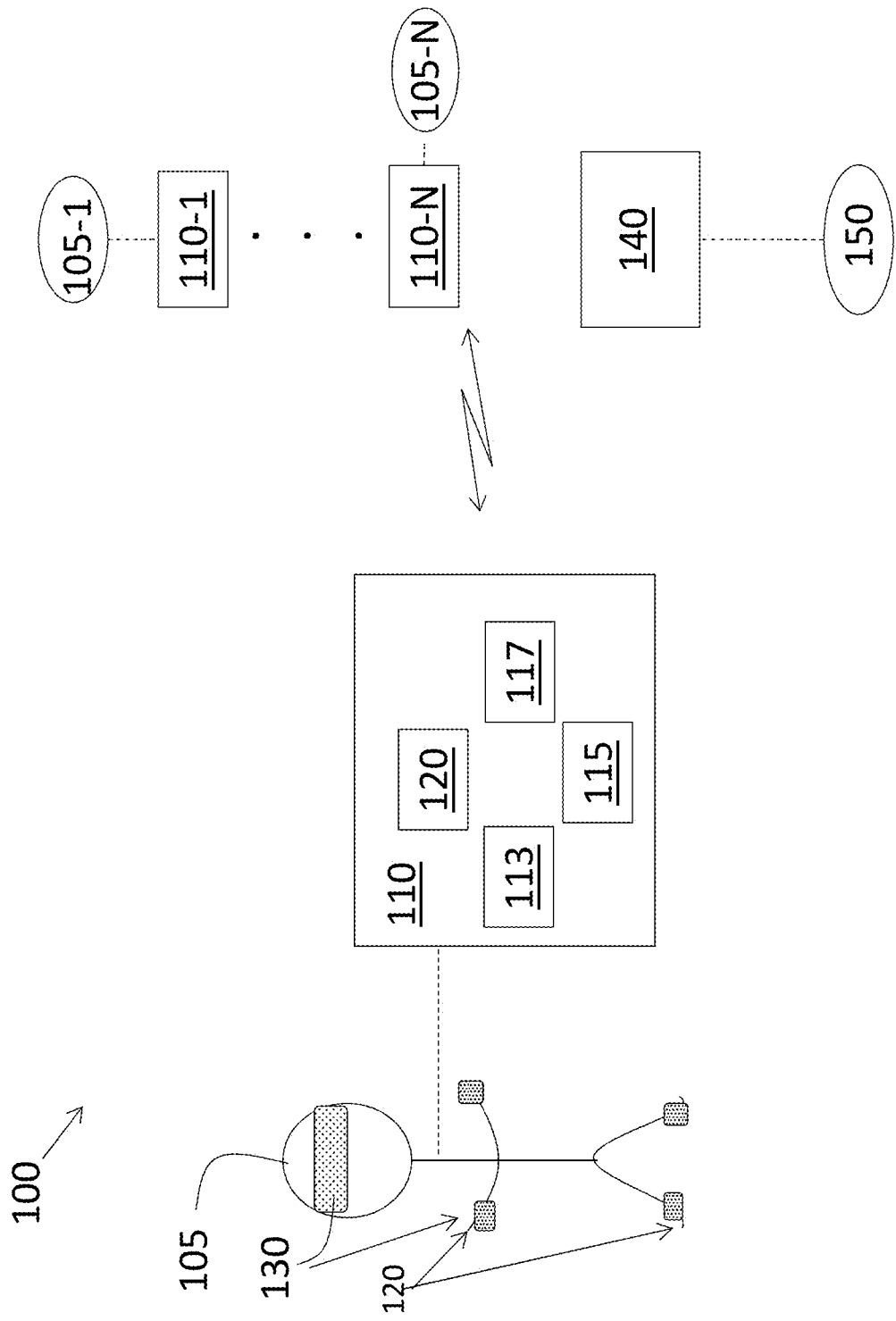
FIG. 1 is a block diagram of a system for remote physical training according to one or more embodiments of the invention.

FIG. 1 is a block diagram of a remote physical training system 100 for performing remote physical training according to one or more embodiments of the present invention. An operator 105 is associated with a virtual reality controller 110. The virtual reality controller 110 communicates with other virtual reality controllers 110-1 through 110-N (where N=any whole number greater than 1) either directly or through a trainer system 140. Each of the other virtual reality controllers 110-1 through 110-N can be associated with another operator 105-1 through 105-N (wherein N=any whole number greater than 1) and corresponding sensors 120 and output devices 130, and the trainer system 140 can be associated with a human trainer 150. For ease of illustration and description, only virtual reality controller 110 and operator 105 are shown in detail. However, the details shown for virtual reality controller 110 and operator 105 apply equally to trainer system 140, trainer 150, virtual reality controllers 110-1 through 110-N, and operators 105-1 through 105-N. Additionally, the descriptions herein of the features and operations of virtual reality controller 110 and operator 105 can apply equally to trainer system 140, trainer 150, virtual reality controllers 110-1 through 110-N, and operators 105-1 through 105-N.

Each virtual reality controller 110 of the remote physical training system 100 can include sensors 120 (e.g., camera), one or more memory devices 113, one or more processors 115, and an interface 117. The memory device 113 can store instructions that are processed by the processor 115 to generate the virtual reality environment that is provided to the operator 105. The interface 117 facilitates input from additional sensors 120 worn by the operator 105, for example, and also facilitates output to the output devices 130 of the operator 105.

Sensors 120 can be worn by the operator 105 or be disposed in the vicinity of the operator 105 as part of or communicatively coupled to the virtual reality controller 110. The sensors 120 can include infrared motion sensors, magnetometers, accelerometers, gyroscopes, inertial sensors, cameras, and other known devices to track eye, head, and body movement of the operator 105. These movements are used to control the output provided to the operator 105 in the virtual reality environment or operators 105 in the group virtual reality environment. Output devices 130 can include visual devices (e.g., the head-mounted display), haptic devices (e.g., vibration sources), and auditory devices (e.g., controlled-pitch sound). For example, tracking eye or head movement of the operator 105 can lead to changes in the portion of the virtual environment that is currently displayed (e.g., when the operator 105 turns her head to the right, the displayed virtual image shifts to the right). The tracked movements of the operator 105 can also be used to obtain feedback.

The interface 117 facilitates communication with other virtual reality controllers 110-1 through 110-N and the trainer system 140, in addition to communication with sensors 120. The interface 117 obtains inputs and provides outputs, including feedback, from the other virtual reality controllers 110 and the trainer system 140. By obtaining information about the movements of other operators 105-1 through 105-N from other virtual reality controllers 110-1 through 110-N, the processor 115 can create a group virtual reality environment. That is, operators 105 and 105-1 through 105-N who are in different physical locations can be presented as avatars in each other's virtual reality environment. Thus, these operators 105 and 105-1 through 105-N can virtually participate in group physical therapy, training, or exercise class, for example. Further, each virtual reality controller 110 and 110-1 through 110-N facilitates a selected virtual environment for each corresponding operator 105 and 105-1 through 105-N. Thus, for example, even though all operators 105 and 105-1 through 105-N participating in a group virtual reality environment are visible to each operator 105 and 105-1 through 105-N, the virtual reality environment (e.g., mountain environment, geometric abstract environment) in which the operators 105 are presented (as avatars) can differ for each operator 105 and 105-1 through 105-N.

By providing movement information to the trainer system 140, the interface 117 can facilitate obtaining feedback from the trainer system 140. The trainer system 140 can include storage of training history for the operator 105 and can additionally store training history for other operators 105. This stored information can facilitate obtaining a baseline for comparison with the progress of the training for the operator 105. For example, the range of motion of the operator 105 can be tracked over the course of training. Progress over time can be compared to baseline progress over time, which is defined from stored information from previous operators 105. If a rate of recovery of an operator 105 deviates significantly (i.e., over a threshold amount) from the expected rate based on group averages, the trainer 150 can be alerted to this discrepancy so that a modification in training can be implemented as needed.

The feedback from the trainer system 140 can be automated based on processing at the training system 140 to compare movements of an operator 105 with an expected sequence of movements. The analysis of the movements can be based on cognitive machine learning analysis, for example. For example, movement information of the operator 105 collected from past sessions such as range of motion, number of repetitions successfully completed, and speed of movements can be correlated through software on a cloud-based computing system with movement information of the operator 105 from the current session to determine how progress compares to predicted performance. The predicted performance can be determined using software incorporating known machine learning algorithms which can include multiple linear regressions, partial least squares, fit, Support Vector Machines, and random forest. The feedback can also be from the trainer 150 associated with the trainer system 140 or a combination of automated and human feedback. In additional embodiments, the storing of movement information and the automated feedback can be performed by the virtual reality controller 110 local to the operator 105.

The processor 115 can generate feedback (e.g., display, vibration, sound) to the operator 105 based on the communication. The feedback can include an adjustment in a routine originally provided to the operator 105 based on the progress or mistakes demonstrated by the avatar of the operator 105 in the virtual environment. The feedback from the trainer system 140 can be real-time feedback and can also include adjustments of future training sessions.

Figure 2:
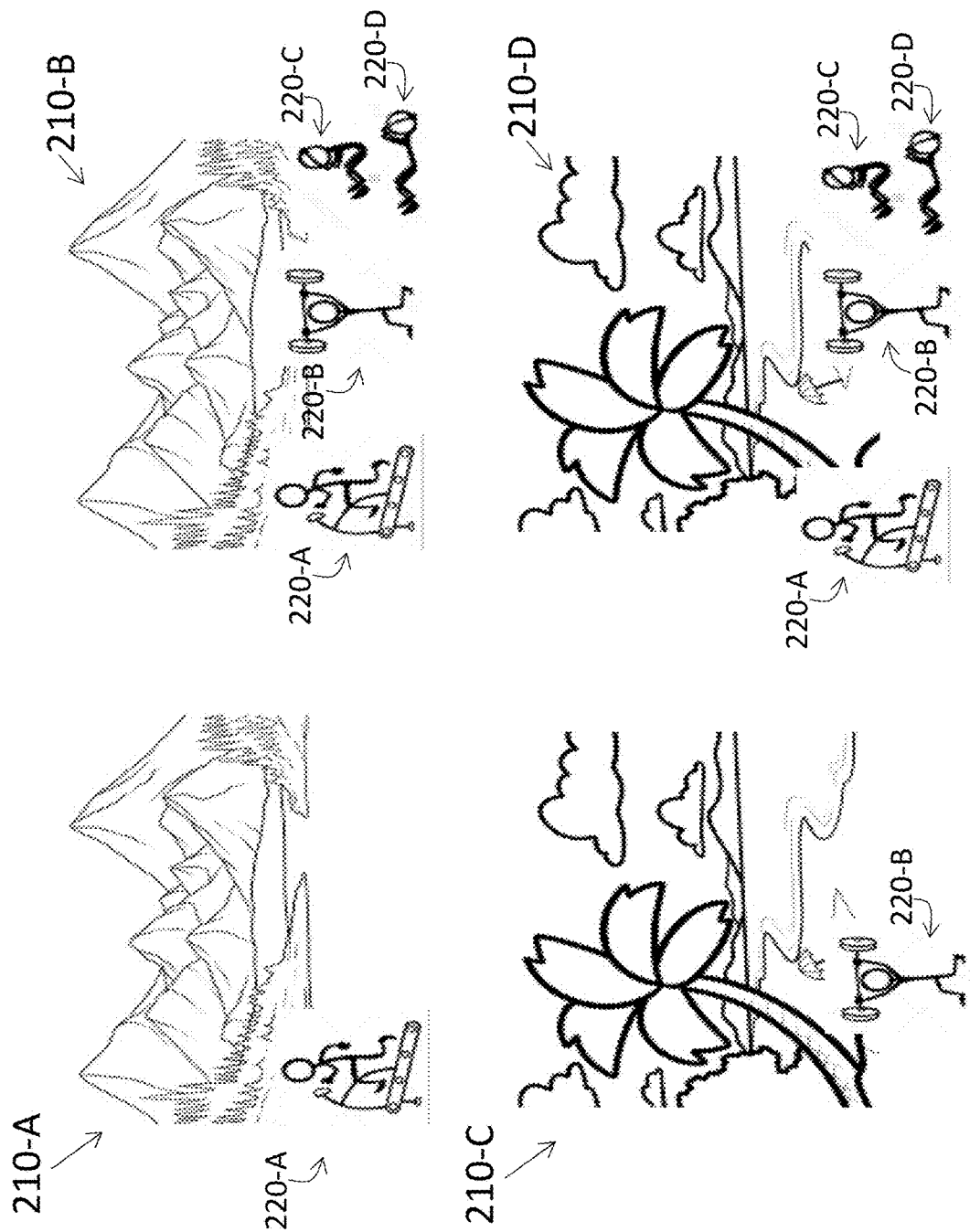
FIG. 2 is an illustration of an exemplary group virtual reality environment according to one or more embodiments of the invention.

FIG. 2 illustrates exemplary virtual reality environments 210-A through 201-D according to one or more embodiments of the present invention. Four exemplary avatars 220-A through 220-D representing four operators 105, 105-1, 105-2, 105-3 associated with four virtual reality controllers 110, 110-1, 110-2, 110-3 are shown. The virtual reality environments 210-A and 210-B are mountainous scenes selected by the operator 105 and provided on an output device 130 (head-mounted display) of the operator 105. In the virtual reality environment 210-A, only the avatar 220-A associated with the operator 105 is displayed based on a selection by the operator 105. In the virtual reality environment 210-B, the avatars 220-A through 220-D associated with the operators 105, and 105-1 through 105-3 are displayed based on the selection by the operator 105.

The virtual reality environments 210-C and 210-D are beach scenes selected by the operator 105-1 and provided on an output device 130 (head-mounted display) of the operator 105-1. In the virtual reality environment 210-C, only the avatar 220-B associated with the operator 105-1 is displayed based on a selection by the operator 105-1. In the virtual reality environment 210-D, the avatars 220-A through 220-D associated with the operators 105, and 105-1 through 105-3 are displayed based on the selection by the operator 105-1. The individual selection of presentations based on a selection at the virtual reality controller 110 associated with a given operator 105 means that the virtual reality environment 220-B can be presented to the operator 105 at the same time that the virtual reality environment 220-D is presented to the operator 105-1, for example.

In the exemplary case shown in FIG. 2, the four operators 105, 105-1, 105-2, 105-3 are physical therapy patients who are receiving real-time feedback from a physical therapist as the trainer 150 (shown in FIG. 1) associated with the trainer system 140 (shown in FIG. 1). Utilizing the group virtual reality environment 220-B, 220-D according to one or more embodiments of the present invention, one or up to all four of the operators 105, 105-1, 105-2, 105-3 can simultaneously perform a physical therapy routine that is different than that performed by the other operators 105, 105-1, 105-2, 105-3 in the group virtual reality environment. Yet virtual group participation can prove motivating for each of the operators 105, 105-1, 105-2, 105-3. In addition, the cost and scheduling with the physical therapist can be easier in the virtual group format described herein than individually.

The physical therapist can see all of the operators 105 in a selected virtual reality environment on her associated trainer system 140.

Utilizing the group virtual reality environment according to one or more embodiments of the present invention, the physical therapist (e.g., trainer 150) can then track progress and provide feedback in real-time as if all the operators 105, 105-1, 105-2, 105-3 and the physical therapist were co-located. The physical therapist can choose to send feedback only to a targeted one of the operators 105, 105-1, 105-2, 105-3. For example, if the targeted operator is operator 105, the feedback is provided from the physical therapist (trainer 150) through the trainer system 140, which communicates with the virtual reality controller 110 of the target operator 105 that provides output to the target operator 105 through one of the output devices 130 of the operator 105. The feedback can be audio output or vibration on the right wrist of the target operator 105, for example. The physical therapist can also choose to provide feedback to two or more operators 105 at once by communicating the feedback to their associated virtual reality controllers 110.

Figure 3:
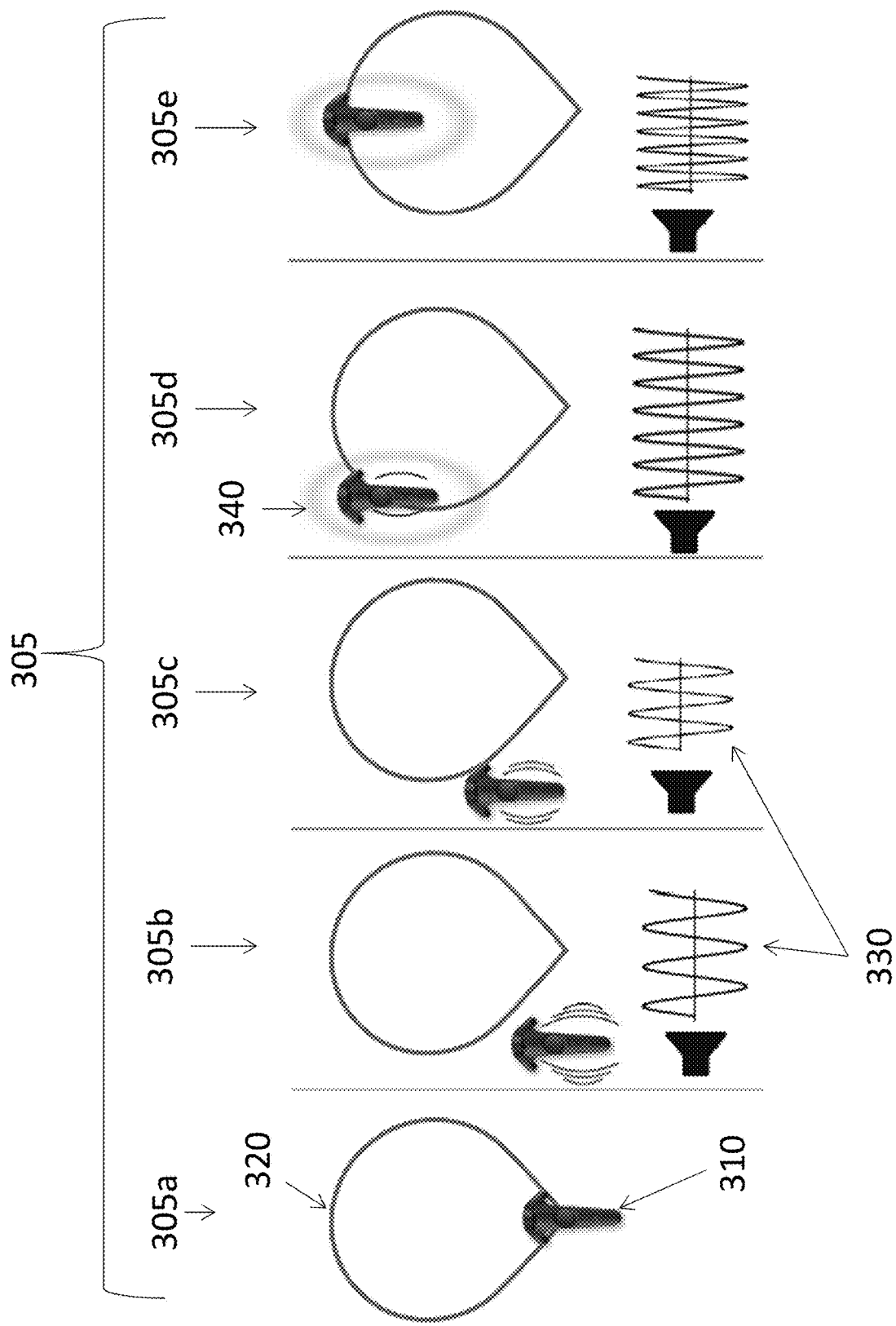
FIG. 3 shows instances of an exemplary training sequence that can be presented and tracked via the system for remote physical training according to one or more embodiments of the invention.

FIG. 3 shows instances of an exemplary training sequence that can be presented and tracked via the system for remote physical training according to one or more embodiments of the present invention. The exemplary training sequence pertains to juggling. The training sequence can be part of a physical therapy routine to improve eye-hand coordination, for example. Referring back to FIG. 1, according to some embodiments of the invention, the virtual reality controller 110 of the operator 105 who is the physical therapy patient can be in communication with a trainer system 140 and human trainer 150. According to some embodiments, the training sequence can be unrelated to any therapy, and the trainer system 140 can provide automated feedback without a trainer 150. In some embodiments, the processor 115 of the virtual reality controller 110 of the operator 105 can provide the feedback itself, without communication with a trainer system 140. Automated feedback from the trainer system 140 or the virtual reality controller 110 can involve known cognitive machine learning analysis, for example.

Returning now to FIG. 3, there are shown five instances 305a through 305e (generally referred to as 305) of images that can be represented graphically to illustrate the training using the exemplary training sequence. For example, the five instances 305 can be displayed to the operator 105 (shown in FIG. 1) or the trainer 150 (shown in FIG. 1) through the output device 130 (shown in FIG. 1). The training sequence defines a path 320 to be traversed by a controller 310 held by the operator 105. The controller 310 is an example implementation of the sensors 120 (shown in FIG. 1). The controller 310 is represented graphically by the controller 310 icon in a virtual reality environment. Three forms of feedback are provided to the operator 105 in the exemplary training. As indicated by FIG. 3, the position of the controller 310 icon is shown relative to the path 320 that is to be traversed. This visual feedback does not require any communication with trainer system 140 or trainer 150, because the operator 105 can see the relative positions of the path 320 and the controller 310 icon in a display (e.g., through a head-mounted display, on a screen, or through another output device 130).

Also shown in FIG. 3 is an icon representing an audio signal 330 associated with instance 305. As the audio signal 330 associated with instances 305b through 305e indicates, the frequency of the audio signal 330 increases as the controller 310 icon gets closer to following the path 320. Thus, the audio signal 330 and, more specifically, the frequency of the audio signal 330 is another form of feedback to the operator 105. The audio signal 330 is generated based on a comparison of the path 320 with the position of the controller 310 icon. This comparison and resulting audio signal 330 can be generated by the trainer system 140 and communicated to the virtual reality controller 110 of the operator 105 or can be generated directly by the processor 115 of the virtual reality controller 110 of the operator 105. The third form of feedback indicated in FIG. 3 is a color change represented by the indicator 340 in instances 305d and 305e. The controller 310 icon can be lit brighter and in a different color when the path 320 is being followed, for example.

By repeating the training sequence with the controller being held by each hand, in turn, the operator 105 can establish the muscle memory required to juggle. A criterion can be established for determining whether the operator 105 has mastered the training sequence. Meeting this criterion can result in an indication being displayed to the operator 105 to attempt to juggle objects. The training sequence can have different phases. For example, once the criterion is met for moving the controller 310 icon along the path 320, training can be added to have the operator 105 squeeze the controller at a particular point in the path 320. This simulates catching a juggled object. When the training sequence is associated with physical therapy and a physical therapist is in the role of the trainer 150, the physical therapist can determine the severity of hand tremors experienced by the patient (operator 105) based on the indications in the virtual reality environment. This type of information (e.g., degree of variation in the controller 310 icon movement from the path 320) can also be automatically logged for each training session.

The criterion for advancing in the training sequence or completing the training sequence can be used to certify the operator 105. For example, operators 105 at remote sites, such as an oil rig, can be trained in certain procedures, such as safety procedures. When the procedure is completed in the virtual reality environment in a way that meets a criterion (e.g., completed within a threshold time within a threshold variation in a set movement pattern), the operator 105 can be certified in that procedure.

Figure 4:
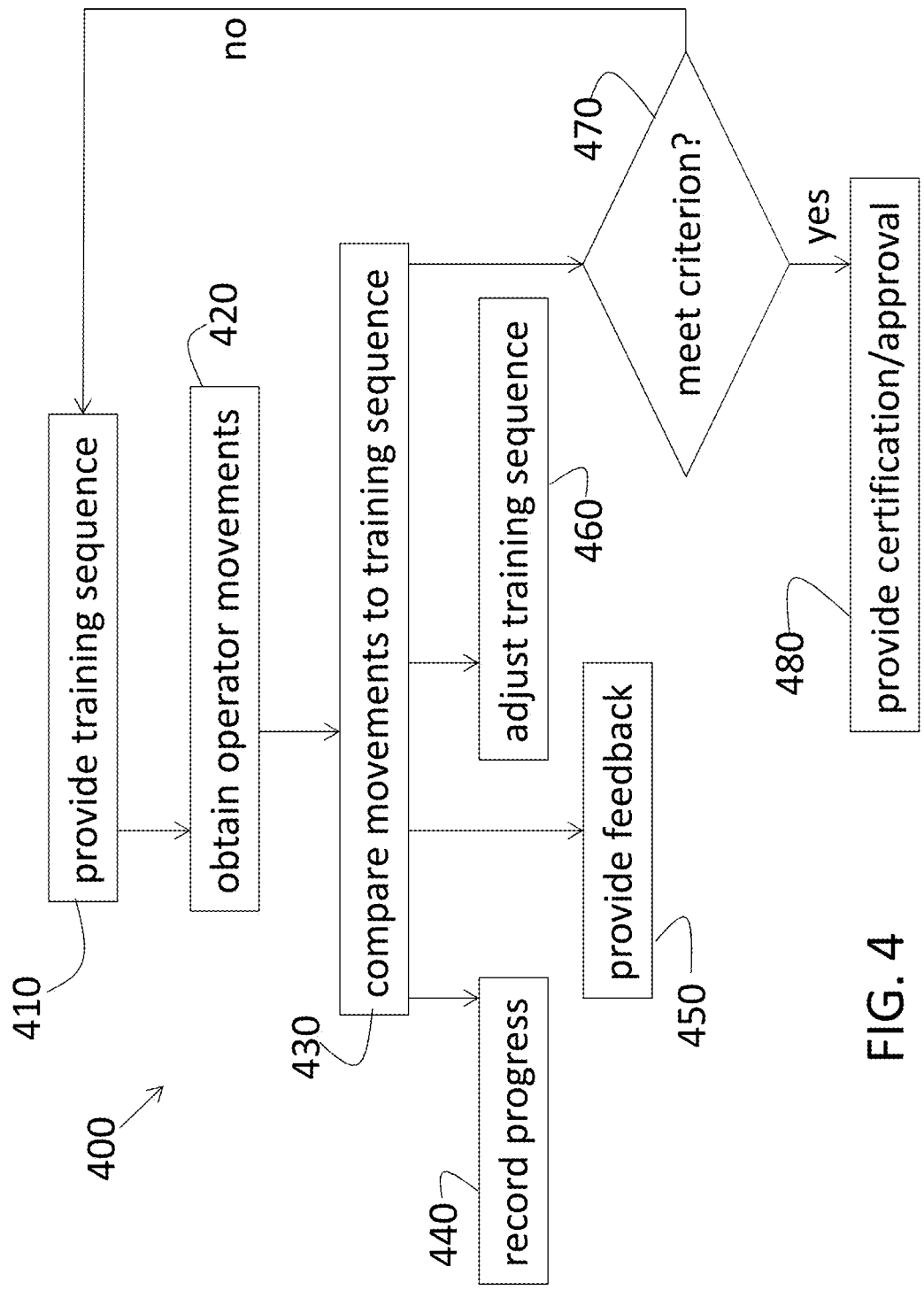
FIG. 4 is a process flow of a method of performing remote physical training according to one or more embodiments of the invention.

FIG. 4 is a process flow of a method 400 of performing remote physical training according to one or more embodiments of the present invention. The training by an operator 105 is remote from a trainer 150 and associated trainer system 140. At block 410, providing the training sequence to an operator 105 in the virtual reality environment can include retrieving the training sequence from the memory device 113 of the virtual reality controller 110 of the operator 105 or obtaining the training sequence through communication with a trainer system 140. Obtaining operator movements, at block 420, includes the sensors 120 measuring various parameters associated with movements made by the operator 105 and using them to animate an avatar of the operator 105 in the virtual reality environment. This virtual reality environment can be modified based on the selection of the operator 105.

At block 430, comparing movements to the training sequence includes comparing the sensor-measured movements of the avatar of the operator 105 in the virtual reality environment with the movements dictated by the training sequence. Recording progress, at block 440, refers to recording the comparison made at block 430 for each training session. Providing feedback, at block 450, refers to the trainer 150 or trainer system 140 or a combination of the two providing one or more forms of feedback to the operator 105 through the virtual environment controller 110 of the operator 105. This feedback can be provided to a group or only one operator 105 within a group in the case of a group virtual reality environment.

Adjusting training, at block 460, refers to determining whether a next training sequence should be provided to the operator 105 based on progress or the training sequence already provided should be slowed down or broken down further based on a lack of progress, for example. Like the feedback (at block 450), the adjustment (at block 460) can be determined by the trainer 150 or trainer system 140 or a combination of the two. The comparison, at block 430, can be used to check whether a criterion has been met, at block 470. The criterion can include a time within which the training sequence is completed or a threshold that must be met in the comparison at block 430, for example. If the criterion is met according to the check at block 470, providing certification or approval to the operator 105 can be performed at block 480. If the criterion is not met according to the check at block 470, providing the training sequence, at block 410, can be repeated according to the exemplary embodiment shown in FIG. 4. In other embodiments, a message can be alternately or additionally provided to the operator 105 or a different entity. Thus, automated certification of a process is facilitated by the remote physical training system according to one or more embodiments.

Figure 5:
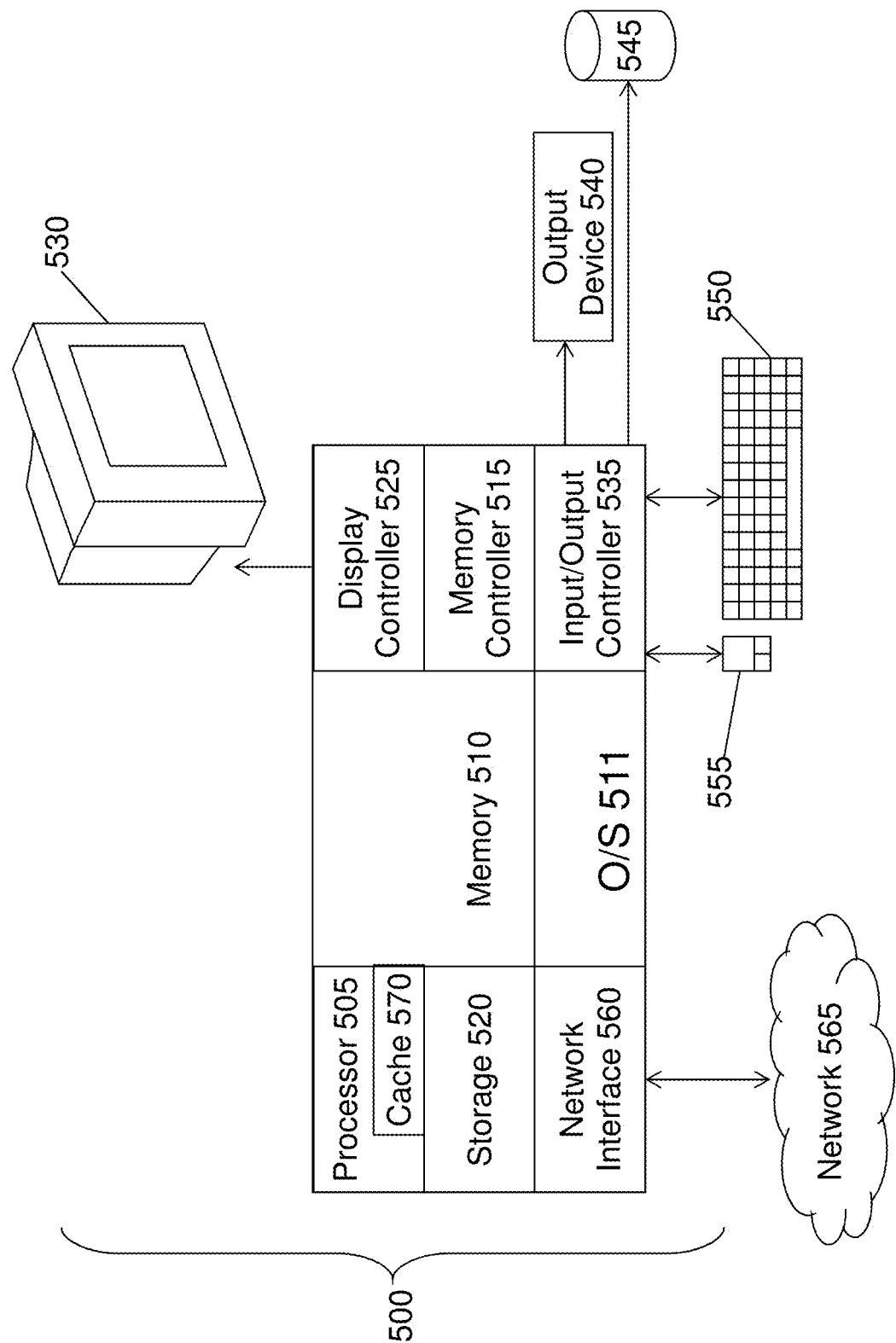
FIG. 5 depicts a computer system capable of implementing aspects of the remote physical training system according to one or more embodiments of the present invention.

FIG. 5 illustrates a block diagram of a computer system 500 for use in implementing the various features and functions of the remote physical training system 100 (shown in FIG. 1) and the method 400 (shown in FIG. 4) according to embodiments of the present invention. The remote physical training system 100 and methods (e.g., method 400) described herein can be implemented in hardware, software (e.g., firmware), or a combination thereof. In some embodiments, the methods described can be implemented, at least in part, in hardware and can be part of the microprocessor of a special or general-purpose computer system 500, such as a personal computer, workstation, minicomputer, or mainframe computer. For example, one or more of the sensors 120, output devices 130, virtual reality controllers 110, and training system 140 can be incorporated within and/or implemented by computer systems 500.

In some embodiments, as shown in FIG. 5, the computer system 500 includes a processor 505, memory 510 coupled to a memory controller 515, and one or more input devices 545 and/or output devices 540, such as peripherals, that are communicatively coupled via a local I/O controller 535. These devices 540 and 545 can include, for example, a printer, a scanner, a microphone, and the like. Input devices such as a conventional keyboard 550 and mouse 555 can be coupled to the I/O controller 535. The I/O controller 535 can be, for example, one or more buses or other wired or wireless connections, as are known in the art. The I/O controller 535 can have additional elements, which are omitted for simplicity, such as controllers, buffers (caches), drivers, repeaters, and receivers, to enable communications.

The I/O devices 540, 545 can further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 505 is a hardware device for executing hardware instructions or software, particularly those stored in memory 510. The processor 505 can be a custom made or commercially available processor, a central processing unit (CPU), an auxiliary processor among several processors associated with the computer system 500, a semiconductor based microprocessor (in the form of a microchip or chip set), a macroprocessor, or other device for executing instructions. The processor 505 includes a cache 570, which can include, but is not limited to, an instruction cache to speed up executable instruction fetch, a data cache to speed up data fetch and store, and a translation lookaside buffer (TLB) used to speed up virtual-to-physical address translation for both executable instructions and data. The cache 570 can be organized as a hierarchy of more cache levels (L1, L2, etc.).

The memory 510 can include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 510 can incorporate electronic, magnetic, optical, or other types of storage media. Note that the memory 510 can have a distributed architecture, where various components are situated remote from one another but can be accessed by the processor 505.

The instructions in memory 510 can include one or more separate programs, each of which comprises an ordered listing of executable instructions for implementing logical functions. In the example of FIG. 5, the instructions in the memory 510 include a suitable operating system (OS) 511. The operating system 511 essentially can control the execution of other computer programs and provides scheduling, input-output control, file and data management, memory management, and communication control and related services.

Additional data, including, for example, instructions for the processor 505 or other retrievable information, can be stored in storage 520, which can be a storage device such as a hard disk drive or solid state drive. The stored instructions in memory 510 or in storage 520 can include those enabling the processor to execute one or more aspects of the enhanced-reality systems 100 and methods of this detailed description.

The computer system 500 can further include a display controller 525 coupled to a monitor 530. In some embodiments, the computer system 500 can further include a network interface 560 for coupling to a network 565. The network 565 can be an IP-based network for communication between the computer system 500 and an external server, client and the like via a broadband connection. The network 565 transmits and receives data between the computer system 500 and external systems. In some embodiments, the network 565 can be a managed IP network administered by a service provider. The network 565 can be implemented in a wireless fashion, e.g., using wireless protocols and technologies, such as WiFi, WiMax, etc. The network 565 can also be a packet-switched network such as a local area network, wide area network, metropolitan area network, the Internet, or other similar type of network environment. The network 565 can be a fixed wireless network, a wireless local area network (LAN), a wireless wide area network (WAN) a personal area network (PAN), a virtual private network (VPN), intranet or other suitable network system and can include equipment for receiving and transmitting signals.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of the invention. For instance, the steps can be performed in a differing order or steps can be added, deleted or modified. All of these variations are considered a part of the claimed invention.

While the preferred embodiment to the invention had been described, it will be understood that those skilled in the art, both now and in the future, can make various improvements and enhancements which fall within the scope of the claims which follow. These claims should be construed to maintain the proper protection for the invention first described.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method of performing remote physical training, the method comprising:
    receiving, using a remotely located processor system, movement of a controller held by an operator resulting from movements performed by the operator who is remotely located from the remotely located processor system;
    presenting, using the remotely located processor system, the movement of the controller held by the operator as movement of an icon representing the controller in the virtual reality environment, and a path to be traversed by the icon in the virtual reality environment; and
    providing real-time feedback on the movement to the operator, wherein the real-time feedback indicates how closely the movement of the icon follows the path to be traversed by the icon.

2. The computer-implemented method according to claim 1, further comprising:
    presenting, using a local processor system that is local to the operator, the movements of the controller by the operator performed by the icon in a local virtual reality environment; and
    the local processor system configuring an appearance of the local virtual reality environment based on a selection of the local virtual reality environment by the operator.

3. The computer-implemented method according to claim 1, wherein the providing the real-time feedback includes providing a change in a frequency of an audio signal or in a color presented in the virtual reality environment based on how closely the movement of the icon follows the path.

4. A computer system configured to perform remote physical training, the computer system comprising:
    a virtual reality controller configured to determine movement of a controller held by an operator and present to the operator movement of an icon representing the controller in the virtual reality environment, and a path to be traversed by the icon in the virtual reality environment; and
    a trainer system, remote from the virtual reality system, configured to provide real-time feedback to the operator through the virtual reality controller of the operator, the real-time feedback indicating how closely the movement of the icon follows the path to be traversed by the icon.

5. The computer system of claim 4, wherein the virtual reality controller is further configured to provide selection to the operator of an appearance of the virtual reality environment in which to have the icon presented.

6. The computer system of claim 4, wherein the real-time feedback includes a change in a frequency of an audio signal or in a color presented in the virtual reality environment based on how closely the movement of the icon follows the path.

7. A computer program product for performing remote physical training, the computer program product comprising a computer readable storage medium having program instructions embodied therewith, the program instructions executable by a processor to perform a method comprising:
    determining movement of a controller held by an operator;
    presenting movement of the controller held by the operator as movement of an icon representing the controller in the virtual reality environment, and a path to be traversed by the icon in the virtual reality environment; and
    providing real-time feedback on the movement to the operator, wherein the feedback indicates how closely the movement of the icon follows the path to be traversed by the icon.

8. The computer program product of claim 7, wherein the method further comprises receiving operator selections that select the virtual reality environment in which to have the icon presented.

9. The computer program product of claim 8, wherein the providing the real-time feedback includes providing a change in a frequency of an audio signal or in a color presented in the virtual reality environment based on how closely the movement of the icon follows the path.

* * * * *